United States Patent [19]

Crocco et al.

[11] Patent Number: 5,741,749
[45] Date of Patent: Apr. 21, 1998

[54] REGENERATION OF A TITANIUM-CONTAINING MOLECULAR SIEVE

[75] Inventors: Guy L. Crocco, Senlis, France; John G. Zajacek, Devon, Pa.

[73] Assignee: Arco Chemical Technology, L.P., Greenville, Del.

[21] Appl. No.: 600,661

[22] Filed: Feb. 13, 1996

[51] Int. Cl.⁶ .......................... B01J 20/34; B01J 38/02; B01J 38/06; B01J 38/10
[52] U.S. Cl. .................. 502/56; 502/34; 502/53; 502/55
[58] Field of Search ................. 502/34, 53, 55, 502/56

[56] References Cited

U.S. PATENT DOCUMENTS

| | | | |
|---|---|---|---|
| 4,833,260 | 5/1989 | Neri et al. | 549/531 |
| 5,270,272 | 12/1993 | Galperin et al. | 502/37 |
| 5,374,747 | 12/1994 | Saxton et al. | 549/531 |
| 5,384,418 | 1/1995 | Zajnuk et al. | 549/531 |
| 5,412,122 | 5/1995 | Saxton et al. | 549/531 |

FOREIGN PATENT DOCUMENTS

| | | | |
|---|---|---|---|
| 3-114536 | 9/1989 | Japan | B01J 21/20 |
| 3114536 | 5/1991 | Japan . | |

OTHER PUBLICATIONS

"Synthesis of Propylene Oxide from Propylene & Hydrogen Peroxide etc.," *Journal of Catalysis* 129 159–167 (1991) M.G. Clerici et al. (no month).

"A Test Reaction for Titanium Silicalite Catalysts", *Catalysis Letters* 2 (1989) 43–48, B. Kraushaar et al. (no month).

"Titanium–Silicalite: A Novel Derivative in the Pentasil Family", G. Perego et al., pp. 129–136, Proc. 7th Intern. Zeolite Confer., (1986) Tokyo (no month).

*Primary Examiner*—Walter D. Griffin
*Assistant Examiner*—Alexander G. Ghyka
*Attorney, Agent, or Firm*—Stephen D. Harper

[57] ABSTRACT

A titanium-containing molecular sieve which has been used as an oxidation catalyst is regenerated to provide a level of performance comparable to that of freshly prepared catalyst by heating in the presence of a gas stream comprised of less than 5 volume percent molecular oxygen. The regeneration temperature may be in the range of from 150° C. to 700° C. The same batch of catalyst thus may be used over an extended period of time in a continuous epoxidation process by periodic practice of the aforedescribed reactivation method.

13 Claims, No Drawings

REGENERATION OF A TITANIUM-CONTAINING MOLECULAR SIEVE

FIELD OF THE INVENTION

This invention relates to a method of restoring the activity and selectivity of a titanium-containing molecular sieve which has been used to catalyze an oxidation reaction such as the epoxidation of an olefin with hydrogen peroxide or other active oxygen species. Regeneration is accomplished by heating the spent catalyst in the presence of a gas stream comprised of less than 5 volume percent molecular oxygen. Contrary to the expectation of the prior art, reactivation is effectively achieved even under anaerobic conditions; the gas stream, for example, may consist essentially of an inert gas such as nitrogen.

BACKGROUND OF THE INVENTION

In recent years, various titanium-containing molecular sieves have been developed which usefully catalyze organic transformations such as the conversion of olefins to epoxides. For example U.S. Pat. No. 4,833,260 discloses the use of TS-1 titanium silicalite in epoxidation wherein hydrogen peroxide serves as a source of oxygen. Heterogeneous catalysts such as titanium silicalite are of great industrial interest, not only because of their high activity and selectivity, but also because such catalysts remain insoluble in liquid phase reaction mixtures and thus can be easily recovered and reused. It would be highly desirable to use titanium-containing molecular sieves in continuous processes. Unfortunately, such materials, for reasons which are not fully understood, tend to slowly deteriorate in performance when used for a long period of time. Due to the relatively high cost of synthesizing this type of catalyst, regeneration of the spent catalyst would be greatly preferred over replacement.

It has previously been proposed to regenerate used titanosilicate epoxidation catalysts by recalcining the catalysts at elevated temperatures in the presence of an oxygen-containing gas. For example, G. Perego et al. *Proc. 7th Intern. Zeolite Confer.*, 1986, Tokyo, p. 827, discloses that a temperature of 550° C. using air as the oxygen-containing gas is sufficient for this purpose. Subsequently, other investigators found that such regeneration could also be accomplished by baking the spent catalyst in a gas atmosphere at temperatures of from 400° C. to 500° C. (Japanese Laid-Open Patent Application No. 3-114536), provided at least 5 volume % oxygen is present.

SUMMARY OF THE INVENTION

We have now discovered that a spent titanium-containing molecular sieve may be reactivated by heating at a temperature of from 150° C. to 700° C. (more preferably, 250° C. to 600° C.) in the presence of a gas stream which contains less than 5 volume percent molecular oxygen. Preferably, the gas stream is passed over the spent catalyst during reactivation. The restoration in catalyst performance was unexpected and surprising in view of the express teaching of the prior art that the presence of at least 5 volume % molecular oxygen is necessary to regenerate catalysts of this type.

DETAILED DESCRIPTION OF THE INVENTION

The titanium-containing molecular sieves which may be regenerated using the process of this invention comprise the class of zeolitic substances wherein titanium atoms are substituted for a portion of the silicon atoms in the lattice framework of a molecular sieve. Such crystalline substances are well-known in the art.

Particularly preferred titanium-containing molecular sieves include the molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), "TS-3" (as described in Belgian Pat. No. 1,001,038), "TS-48" (having a ZSM-48 structure), and "TS-12" (having an MTW-type structure). Also suitable for use are the titanium-containing molecular sieves having framework structures isomorphous to zeolite beta as well as those materials designated "CIT-1", "SSZ-33", "ETS-4", "ETS-10", and "Ti-MCM-41". The titanium-containing molecular sieves preferably contain no non-oxygen elements other than titanium and silica in the lattice framework, although minor amounts of boron, iron, aluminum, and the like may be present. Titanium-containing molecular sieves usable in the present regeneration process are sometimes variously referred to by workers in the field as "titanium silicalites", "titanosilicates", "titanium silicates", "silicon titanates" and the like. The molecular sieve may be admixed with a binder or other matrix material and may be in any physical form such as powder, pellets, granules, blocks, or the like. Supported titanium-containing molecular sieves such as titanium silicalite supported on titania, silica, or the like may also be regenerated in accordance with the invention.

Titanium-containing molecular sieves suitable for use in the process of this invention will generally have a composition corresponding to the following empirical formula $xTiO_2:(1-x)SiO_2$, where x is between 0.0001 and 0.500. More preferably, the value of x is from 0.01 to 0.125. The molar ratio of Si:Ti in the lattice framework of the titanium-containing molecular sieve is advantageously from 9.5:1 to 99:1 (most preferably, from 9.5:1 to 60:1). Large pore (mesoporous) as well as small pore (microporous) molecular sieves are suitable for use. Relatively titanium-rich molecular sieves may also be successfully regenerated. It has been found that spent titanium-containing molecular sieves typically are contaminated with organic substances, possibly polymeric or oligomeric in character, which are not present in fresh catalyst. The regeneration process herein described is capable of reducing the levels of such contaminants, as indicated by a decrease in the % C present by elemental analysis.

Prior to regeneration, the titanium-containing molecular sieve will have been used to catalyze some desired synthetic process. The present method is particularly useful for restoring the activity and selectivity of a catalyst employed in olefin epoxidation. Such epoxidation processes are well-known (see, for example, U.S. Pat. Nos. 4,833,260, 5,354,875, 5,262,550, 5,214,168, 5,374,747, 5,384,418, and 5,412,122) and may be performed using a variety of olefins as well as different types of oxidizing agents. For example, the catalyst to be regenerated may have been recovered from a process wherein propylene is converted to propylene oxide using hydrogen peroxide. Without wishing to be bound by theory, it is believed that the by-products which tend to accumulate on the catalyst during epoxidation (e.g., epoxide oligomers, olefin oligomers) are capable of being converted by degradation to more volatile and/or more soluble substances at relatively low temperatures. Apparently, for reasons which are not well understood, such degradation does not require the presence of oxygen.

The spent titanium-containing molecular sieve is preferably separated in solid form from any liquid components of the reaction mixture in which it may be present prior to regeneration. For example, where the molecular sieve has been deployed in the form of a slurry, it may be readily collected by filtration, centrifugation, decantation, or other such mechanical means and then transferred into a vessel which is suitable for carrying out the regeneration. Alternatively, where the molecular sieve has been used as a fixed bed, the liquid components may be simply drained or pumped away from the spent catalyst and regeneration conducted in the same vessel as the catalytic process. It is not, however, necessary to completely dry the recovered catalyst prior to regeneration since any minor amounts of solvent, reactants, and the like adsorbed on the catalyst can be readily removed and disposed of during such regeneration. An important advantage of the present method is that reactivation of catalyst may be performed in vessels of the type conventionally used for olefin epoxidation. Prior art regeneration processes utilizing oxygen and calcination temperatures in excess of 400° C. may need to be carried out in specialized equipment fabricated using relatively high cost materials of construction in order to avoid metallurgical complications.

The spent titanium-containing molecular sieve is heated in the presence of a gas stream at a temperature of from 150° C. to 700° C. The temperature range of from 250° C. to 600° C. is especially suitable. No significant loss in the crystallinity of the molecular sieve is observed. The temperature may be kept constant during regeneration or may be periodically or continuously increased or decreased as may be desired. It has unexpectedly been found that the presence of molecular oxygen in the gas stream is not needed in order to accomplish satisfactory reactivation of the molecular sieve. That is, the gas stream may be comprised predominantly of one or more inert gases such as nitrogen, helium, carbon dioxide, argon, water vapor or the like and mixtures thereof. The gas stream thus contains less than 5 volume % oxygen. The process of the invention is capable of accomplishing its intended purpose (i.e., catalyst reactivation) even when the gas stream contains 1 volume % $O_2$ or less. Anaerobic (oxygen-free) regeneration conditions may also be employed, if desired.

The process may be conducted such that the gas stream is continually passed over the titanium-containing molecular sieve in order to sweep away any volatile products evolved from the catalyst. Alternatively, the regeneration may be performed in a discontinuous or static manner. That is, a volume of gas may be introduced into the regeneration vessel containing the spent catalyst, the vessel sealed and heated for some period of time before discharging the gas and replacing it with a fresh volume of gas. The catalyst is heated for such time as may be necessary to restore the desired level of activity and selectivity. Typical heating times are from 1 to 150 hours. The optimum time will vary somewhat depending upon the extent to which the catalyst has been deactivated, the type of reaction in which the catalyst has been used, the regeneration temperature, the flow rate of gas through the catalyst, as well as other factors, but may be readily ascertained by routine experimentation. A useful method of monitoring the extent of regeneration is to measure the % C present in the catalyst by elemental analysis. A spent catalyst will typically contain 1 weight % carbon or more, with a regenerated catalyst generally having less than 1 weight % carbon. Broadly speaking, it will usually be desirable to heat the spent catalyst under conditions effective to reduce the residual carbon level by at least 50% (more preferably, at least 85%) relative to the residual carbon level in the unregenerated catalyst. Activities and selectivities comparable to that of freshly prepared titanium-containing molecular sieves may be attained even with only relatively modest decreases in carbon levels however. Although the regeneration may be performed at any pressure, atmospheric or subatmospheric pressures are preferred.

Following heat treatment, the regenerated molecular sieve may be further treated if so desired to further modify its catalytic properties. For example, the catalyst may be treated with a basic substance or a silylating agent to neutralize acidic sites which may be present. Washing with a suitable solvent such as water and/or an organic solvent such as an alcohol or the like may also be performed. The regenerated catalyst may be admixed with freshly prepared catalyst prior to reuse, if so desired.

EXAMPLES

Two portions of spent TS-1 titanium silicalite catalyst which had been used for olefin epoxidation were heated for 28 hours at 385° C. in the presence of, in one run (for comparative purposes), a flowing air stream, and in a second run (to illustrate the process of the invention), a flowing nitrogen stream. In both runs, removal of carbon from the catalyst was essentially quantitative as determined by elemental analysis.

We claim:

1. A method for regenerating a spent titanium-containing molecular sieve which has framework titanium atoms and has been employed in an olefin epoxidation process wherein propylene is converted to propylene oxide using hydrogen peroxide comprising heating the spent titanium-containing molecular sieve at a temperature of from 150° C. to 700° C. in the presence of a gas stream which is free of molecular oxygen for a time effective to enhance the activity of the spent titanium-containing molecular sieve.

2. The method of claim 1 wherein the spent titanium-containing molecular sieve has an MFI, MEL, or zeolite beta topology.

3. The method of claim 1 wherein the regeneration is performed in a static manner.

4. The method of claim 1 wherein the temperature is from 250° C. to 600° C.

5. The method of claim 1 wherein the regeneration time is from 1 to 150 hours.

6. The method of claim 1 wherein the gas stream is passed over the spent titanium-containing molecular sieve during the regeneration.

7. The method of claim 1 wherein the gas stream is comprised of one or more inert gases selected from the group consisting of nitrogen, helium, carbon dioxide, argon, water vapor, and mixtures thereof.

8. The method of claim 1 wherein the spent titanium-containing molecular sieve has the composition $xTiO_2:(1-x)SiO_2$ where x is from 0.01 to 0.125.

9. A method for regenerating a spent titanium-containing molecular sieve having an MFI, MEL, or zeolite beta topology and framework titanium atoms and has been used in an olefin epoxidation reaction wherein propylene is converted to propylene oxide using hydrogen peroxide comprising heating the spent titanium-containing molecular sieve at a temperature of from 250° C. to 600° C. in the presence of a flowing gas stream which is free of molecular oxygen for a period of from 1 to 150 hours.

10. The method of claim 9 wherein the flowing gas stream consists essentially of nitrogen.

11. The method of claim 9 wherein the spent titanium-containing molecular sieve has the composition $xTiO_2:(1-x)SiO_2$ where x is from 0.01 to 0.125.

12. The method of claim 9 wherein the spent titanium-containing molecular sieve has been deployed in the form of a fixed bed within a reactor vessel during said olefin epoxidation reaction.

13. The method of claim 9 wherein regeneration of the spent titanium-containing molecular sieve is performed within said reactor vessel.

* * * * *